United States Patent
Ansari

[11] Patent Number: 5,984,863
[45] Date of Patent: Nov. 16, 1999

[54] PEDIATRIC LARYNGOSCOPIC BLADE

[76] Inventor: Mohammed A. Ansari, 2349 White Oak, Wichita, Kans. 67207

[21] Appl. No.: 09/079,708

[22] Filed: May 15, 1998

[51] Int. Cl.[6] .................................................. A61B 1/26
[52] U.S. Cl. ........................... 600/185; 600/190; 600/240
[58] Field of Search ................................... 600/185, 186, 600/187, 188, 189, 190, 191, 192, 193, 194, 195, 196, 240, 210

[56]  References Cited

U.S. PATENT DOCUMENTS 1,396,933  11/1921  Jacoby ..................................... 600/240
5,776,053  7/1998  Dragisic et al. ......................... 600/195

*Primary Examiner*—Beverly M. Flanagan
*Attorney, Agent, or Firm*—Bradley P. Sylvester

[57] ABSTRACT

An improved laryngoscope blade, where the lingual side of the blade, being the side that is presented against a patient's tongue during examination, defines a concave area which defines a cavity which allows the patient's tongue to be cradled during the examination, and where the curved descending sides of the blade proiaote and urge the tongue into the cavity area, and prevent the tongue from flattening out sufficiently so as to curve over onto the top side of the blade, where the view of the patient's airway would be obstructed.

7 Claims, 3 Drawing Sheets

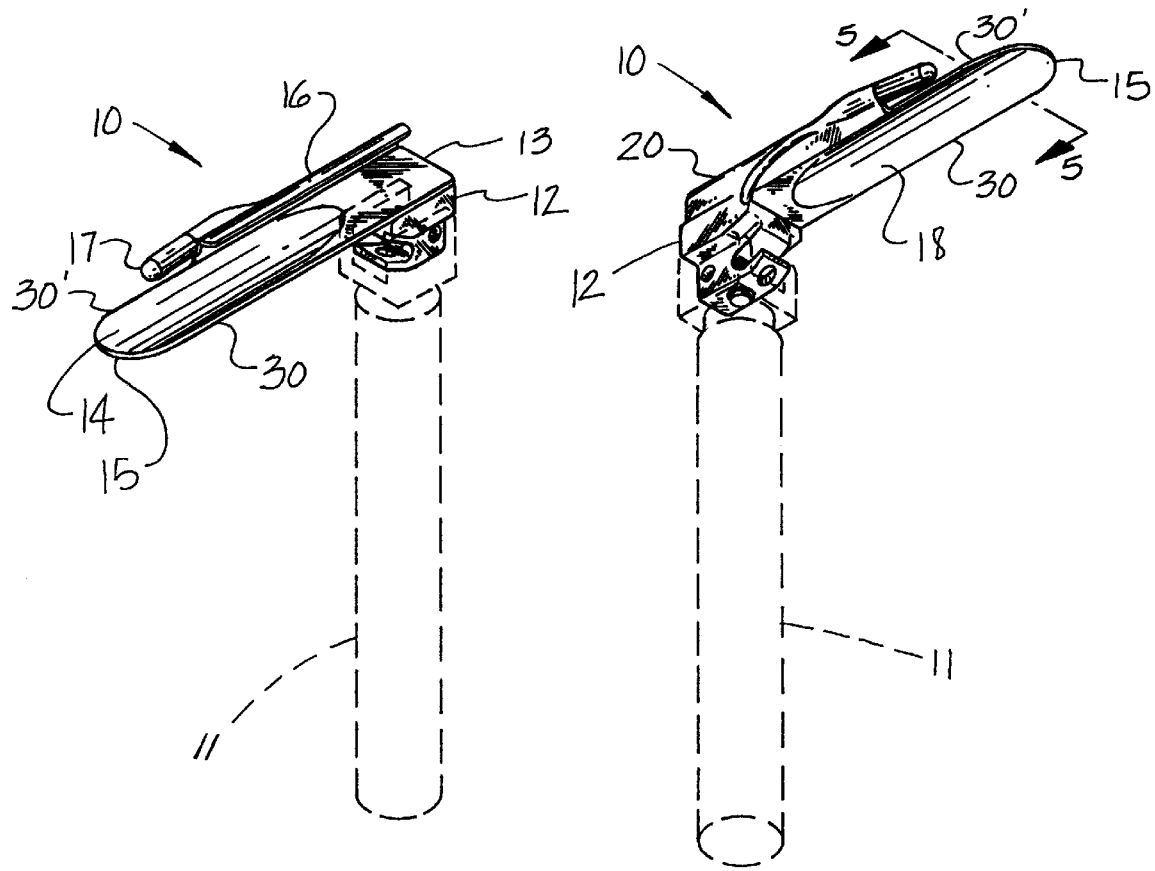

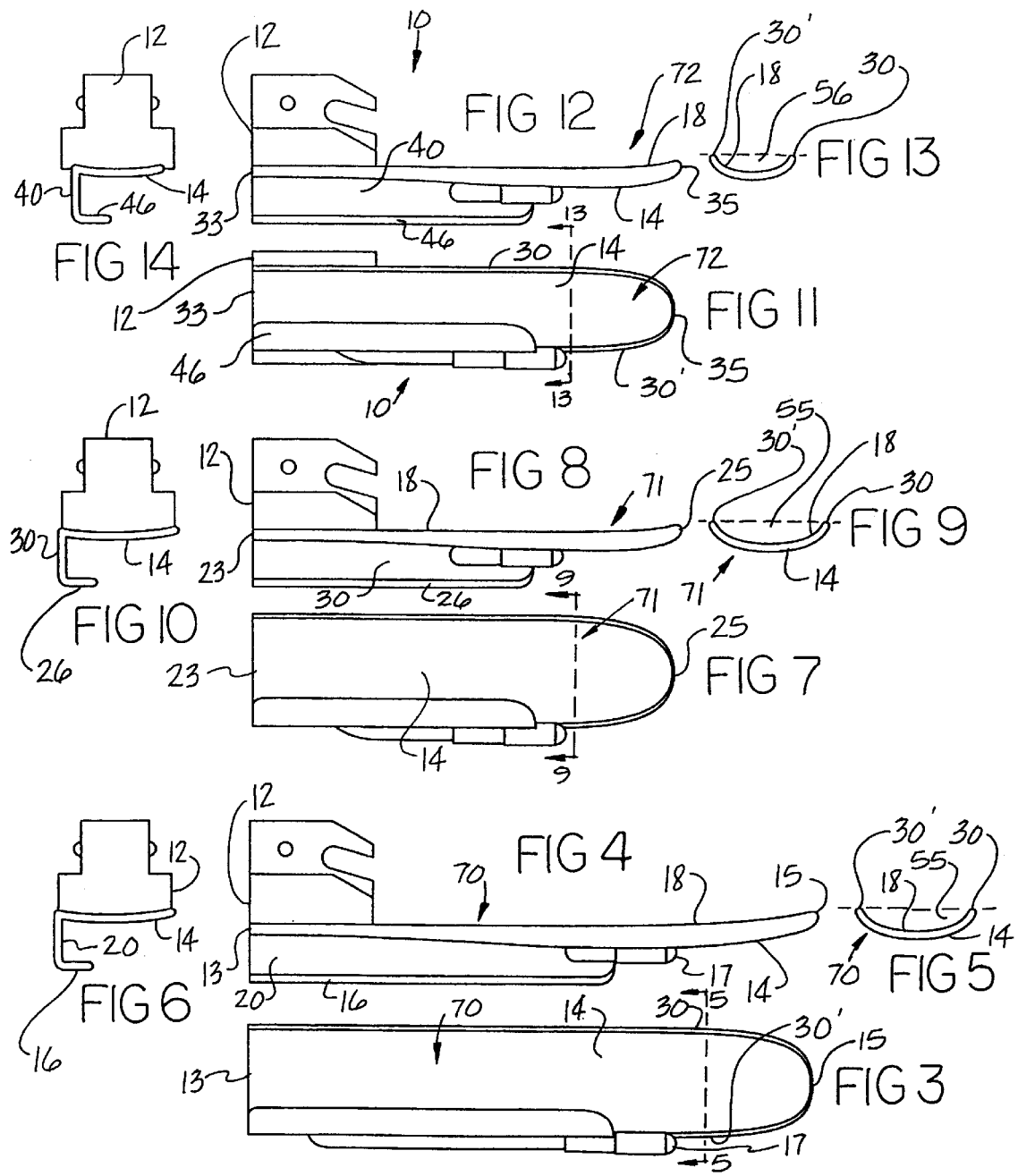

PEDIATRIC LARYNGOSCOPIC BLADE

BACKGROUND OF THE INVENTION

Referring to U.S. Pat. No. 5,003,962 (Choi), a laryngoscope with a double angle blade is shown. This scope was an improvement on prior art, due to the angles that were defined by the blade. This particular blade had a first angle of approximately 20 degrees, and a second angle, farther along the length of the blade, of approximately 30 degrees. The blade itself had no curvature, but rather was comprised of three separate segments, with the length of each segment defined by a bent portion. This blade relied on the angle segments to adequately keep the person's tongue out of the way during examination, rather than rely on any scallops or curved areas on the blade, as prior art blades had done.

Referring now to U.S. Pat. No. 510,516 (Nithack) exemplifies a means to illuminate a patient's throat. This patent, having been issued in 1893, exemplifies some of the prior art regarding this type of instrument. The blade of this instrument had a longitudinal groove which was placed on the upper side of the person's tongue. The blade itself was flat, with the exception of the hollow groove or ribbon.

Referring now to U.S. Pat. No. 330,139 (Meyer), a scope is shown having a similar intended use. The blade of this particular invention defined a curved surface, however the curvature was defined along the length of the blade and not across the width of the blade. The illumination of a person's mouth, along with holding down their tongue, was the chief utility of this invention. Basically, the blade of this invention did nothing more than attempt to hold a portion of the tongue out of the way of a beam of light. The extent to which a person's tongue would be held out of the way was questionable, and did not seem to be the chief focus of this invention.

Referring now to U.S. Pat. No. 5,575,758 (Easterbrook), where the inventor in this patent paid particular attention to improving the blade used with a scope. The blade itself provided a gentle curved slope along its length, and had a spatula portion, and flange portion. This particular invention however, makes no improvements as to actually restricting the edges of a person's tongue from overlapping or protruding over the sides of the blade, such as would be available through the use of a concave surface being presented to a person's tongue.

Referring now to U.S. Pat. No. 5,529,570 (Storz), a prior art spatula or blade is shown. This particular invention provides for an improved light placement, along with providing a curb on the spatula shaped portion, which is intended to restrict movement of a person's tongue. The surface of the spatula blade is curved along the length, but is flat with regard to the area from side to side of said spatula blade. This particular invention lacks the optimal ability to restrict a person's tongue from protruding over the edges of the spatula blade and assisting in restricting the observable illuminated area of the patient.

Referring now to U.S. Pat. No. 4,947,896 (Bartlett), a scope is shown having a plurality of channels running along the length of the blade. In this invention, various tubes are provided with passageways along full length of the blade. Surface 20 presents a partial convex surface against a person's tongue, which actually promotes and encourages the tongue to spill over the sides of the blade and obstruct the viewing area. There is no adequate cavity defined by the blade which would assist in preventing the tongue from flattening out or widening so that it would not come over the edge of the blade.

Referring now to U.S. Pat. No. 4,834,077 (Sun), a disposable sheath is shown, which is usable with the blades described in various patents, and used in the field of medicine. The sheath itself has a design whereby an extreme curvature in a shown from side to side of the sheath, promoting a concave service on one side and a convex service on the other side of said sheath. In this patent, the concave side is not intended to come into contact with the patient's tongue. Rather the convex surface of the sheath, which is fitted over a similarly shaped blade, is the area of contact. This particular curvature does not inhibit the tongue from spreading out and curbing over the sides of the blade. The convex surface actually promotes and encourages the tongue to flatten out.

Referring now to U.S. Pat. No. 5,665,052 (Bullard), recent improvements with respect to laryngoscopes are shown. This particular invention dealt with the problems where tubes that were not properly positioned would not pass between the vocal cords. In the blade portion of this particular scope, the curvature appears to be only along the length of the blade. There is no concave surface presented to the surface of the patient's tongue, other than the curvature along the blade length. This invention appears to have used during surgical procedures, rather than for routine examination, and the blade portion would normally be inserted farther into the oral cavity and throat than would be required in a routine examination.

Prior art has attempted to overcome visual blockage that often accompanies examination using this device. While prior devices have shown a multitude of blade configurations, the prior blades have not adequately discouraged encroachment of the patient's tongue around and over the sides of the blade. The prior art blades have failed to manipulate a patient's tongue in any manner other than longitudinally, and have ignored the problems inherent with a tongue widening or flattening out, thereby allowing the tongue to wrap itself around the sides of the blade itself. This causes significant loss of the area able to be viewed, and those interferes with optimal patient treatment.

SUMMARY OF THE INVENTION

There are significant anatomic differences in the airway of the infants, as compared to adults. The airway size is smaller, the tongue is relatively larger, and there is a relatively larger size of head. In addition, there are different cervical spinal curvature, and infants tend to have shorter necks, which makes the long axis of the airway different from that of an adult.

In infants, the position of the larynx is relatively higher, and the vocal cords are attached lower and anteriorly. The narrowest part of the airway is below the vocal cord at the level of cricoid cartilage and it is non distensible. The shape of larynx is triangular compared to that of an adult, which is cylindrical. The epiglottis is shorter, narrower and angled away from the long axis of the trachea.

The major obstacles for successful neonatal intubations is the displacement of the tongue during intubation obstructing the glottic view. The lingual surface of the current laryngoscope blade is convex and it is narrower in width which is not consistent with the neonatal tongue anatomy. The current laryngoscope blade can not hold and lift the tongue properly during intubation. The tongue will often slip and obstructs the glottic view, thus complicating intubation.

In addition, the shorter epiglottis is difficult to lift, and obscures the glottic view. Further, the smaller size of the oral cavity in the neonates, and the anterior location of the vocal cords make it more difficult to pass the endotracheal tube in to glottic opening. It is also difficult to align the visual and the long axis of the airway because of the unique anatomy in the neonates.

In order to improve success of neonatal intubation and reduce the number of attempts to intubate successfully, the invention described below was created. The blade is wider, and the lingual surface of the blade is concave from side to side. The shape of the blade is more consistent with the neonatal tongue anatomy, and will hold and lift the tongue better than the current blade.

This improved laryngoscope has incorporated into it's improved blade, a shape that better facilitates manipulation of a patient's tongue during oral and airway examination. During examination of a person's airway, the user of the laryngoscope will grasp it by an elongated handle, and manipulate the blade or spatula portion of this device into the patient's mouth. Attached to the blade is a light emitting device, which serves to illuminate the interior of the person's throat and airway.

The purpose of the blade, is mainly to prevent the tongue of the person being examined from interfering with making a visual determination, or blocking the view of the insertion of an endotracheal tube into the airway. The blade therefore, must have a sufficient width so as to cover a substantial portion of the tongue. The length of the blade must be sufficient so that the tongue is able to be urged out of the way, from the front of the mouth to the back of the throat region.

While prior art blades have generally presented a convex or flat surface against the upper side of a person's tongue during examination, this improved device presents a concave depression against the tongue, with the sides of the improved blade oriented so that they curved downward around the sides of the tongue. This blade has the benefit of urging the tongue sides inward, so as to promote and urge the tongue to fill the concave depression area, which best minimizes the flattening out aspects of a person's tongue.

This improved blade has the additional benefits of virtually gripping the tongue, using the descending sides that are curved around the tongue, so that sideways or lateral movement of the blade in a person's mouth will generally continue to restrict movement of the tongue in the same manner. In effect, there is very little slippage or movement of the blade sideways on a person's tongue, even though the blade portion itself is being moved from side to side. This sideways movement may be necessary to give optimal observation during a medical treatment.

Since treatments involving a person's airway often require quick action and minimal delays, this improved blade allows the person examining a patient to effectively immobilize the patient's tongue, so that a constant unobstructed view is able to be had of the airway.

Accordingly, it is on intention of this invention to provide an improved blade for use with laryngoscopes during the examination and treatment of patients, which more effectively restricts intrusion of the tongue into the examination viewing area.

Accordingly, is a further intent of this invention to provide a means to control the spreading or flattening out of a person's tongue during visual examination of the airway.

Accordingly, it is a further intent of this invention to offer a device which is able to maintain restriction of the patient's tongue, while a laryngoscope is being manipulated from side to side within a patient's mouth.

BRIEF DESCRIPTION OF THE DRAWINGS

FIG. 1 is a perspective view of the improved blade, where the top side of the blade exhibits a convex surface.

FIG. 2 is a perspective view of the improved blade, where the bottom side of the blade shown, exhibits a concave surface.

FIG. 3 is a top view of the improved blade, where the blade shown is elongated.

FIG. 4 days depicts a side view of the improved blade, where the blade being shown is elongated.

FIG. 5 is a cross-sectional view of the elongated blade shown in FIGS. 3 and 4.

FIG. 6 is a back view of the blade and coupling.

FIG. 7 is a top view of the improved blade, where the blade being shown is of a standard length for use with children.

FIG. 8 is a side view of the improved blade, where the blade being shown is of a standard length for use with children.

FIG. 9 is a cross-sectional view of the blade shown in FIGS. 7 and 8.

FIG. 10 is a back view of the blade shown in FIGS. 7, 8 and 9, where the blade is fixed on a coupling.

FIG. 11 is a top view of a narrow blade.

FIG. 12 is a side view of the narrow blade.

FIG. 13 is a cross sectional view of the blade shown in FIG. 11 and FIG. 12.

FIG. 14 is a back view of the blade shown in FIGS. 11, 12 and 13, where he blade is fixed on a coupling.

DETAILED DESCRIPTION OF THE INVENTION

Referring now to FIG. 1 and FIG. 2, the improved curved blade 70 of the laryngoscope 10 is shown mounted on a coupling 12. The blade 70 is generally a separate piece from the coupling 12, where the coupling 12 is able to fit into the handle 11, and where said handle 11 is able to be held by a person using this invention. Use of the handle 11 to position the angle of the blade 70 into a person's mouth and throat region, is likewise a preferred method. The coupling 12 is able to fit firmly into the receiving area on the handle 11. The blade 70 is firmly fixed to be coupling 12 so that the orientation of the blade 70 is able to be guided and controlled by manipulation of the handle 11.

Figure 16:
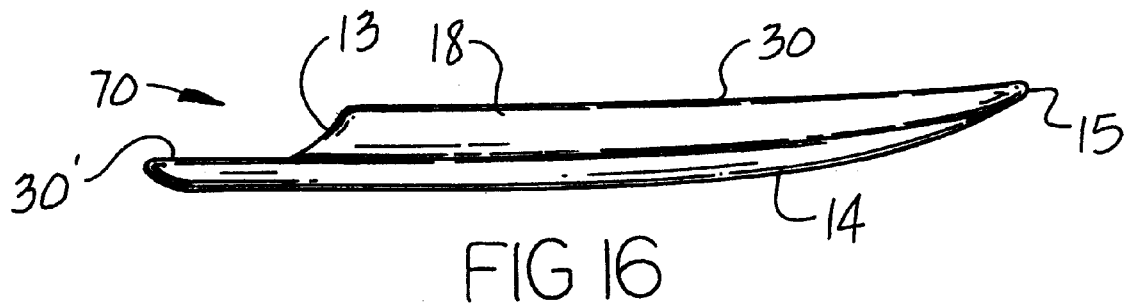
FIG. 16 is a perspective view of the improved blade, showing the concave cavity area and curvature of the blade.

Referring also to FIG. 16, the blade 70 is comprised of a spatula like shape, in which the base end 13 is able to be fixed to coupling 12, so that the blade 70 is preferably fixed in relationship to be coupling 12, in order to allow the blade 70 and coupling 12 to effectively move together as a single piece. The blade 70 itself may be removable from the coupling 12, if so designed, however in most instances, and preferably, the blade 70 and coupling 12 are securely welded or fixed together.

Along the length of the blade 70, the sides 30 and 30' are generally parallel to one another, so as to define a blade 70 having a constant width along its length. The front end 15 of blade 70 defines a generally curved edge, also having a generally smooth surface between the palatal surface 14 and lingual surface (also referred to as the "lingual" side) 18 of blade 70, so as not to cause abrasion on sensitive tissues in a patient's airway.

The blade 70 and coupling 12 are able to fit onto handle 11, where the coupling 12 and handle 11 defined a means to attach the two said pieces together. The coupling 12 shown in the drawings, is one example of the typical or standard coupling 12 used with laryngoscopes. Where said blade 70 is fixed to coupling 12, the orientation of blade 70 will be approximately at a ninety degree angle from the handle 11, when the blade 70 and coupling 12 are attached to handle 11.

Use of this laryngoscope 10, is accomplished by gripping handle 11, and inserting blade 70 into a patient's mouth. The orientation of the blade 70, with handle 11, allows the person doing the examination to hold handle 12, with the blade 70 able to be inserted at a near ninety degrees, or directly into the mouth and back of the throat.

Referring also to FIG. 3, a top view of blade 70 is shown. As is seen in FIG. 3, the elongated blade 70 has a fairly uniform width along its length, as defined from side 30 to side 30'. Oriented above the palatal surface 14 of blade 70, is a structure to hold a light emitting means 17 in place. As it is also shown in FIG. 4 and FIG. 6, a flange 20 protrudes upward at a ninety degree angle from the palatal surface 14 of blade 70. Flange 20 has a curved end, where the degree of curvature is also approximately 90 degrees, so as to define a guide flange 16. The blade 70, flange 20, and guide flange 16 define and area which allows a tube (not shown) to be inserted along the length of the blade 70 while it is positioned in a person's airway.

Flange 20 and guide flange 16 extend outward and upward from the palatal surface 14 of blade 70 for a distance of approximately 65 percent along the length of blade 70. This means that where blade 70 has a length of approximately 10 cm, the flange 20 and guide flange 16 will have a length of approximately 6.5 cm. Using these dimensions, the height of flange 20, is approximately 0.7 cm, with guide flange 16 having a width of approximately 0.5 cm. These measurements would be fairly accurate where the blade 70 has a width of approximately 2.0 cm. The widths and lengths described above, should not be construed as the only measurements available for this type of invention. Since many dimensions of widths and length are permissible, all measurements given above may vary, as example by the discussion of several additional blade dimensions shown below.

Referring also to FIG. 5, the cross-sectional view of blade 70 is shown. A cross sectional view is shown along plane 60, as shown in FIG. 3, which exhibits and defines the curvature of the palatal surface 14 and lingual surface 18 of blade 70. A cross sectional view, as shown in FIG. 5, depicts side 30 and side 30' as defining the ends of the curved blade 70 width, in which the lingual surface 18 exhibits a concave surface, and where palatal surface 14 exhibits and defines a convex surface. As it is shown in FIG. 4, the degree of convex and concave curvature defined by the blade surfaces 14 and 18 increases slightly along the length of said blade 70, moving from the base end 13 toward the front end 15. The greatest degree of curvature exhibited by blade 70, is in the area of length towards the front end 15, where the degree of curvature remains approximately constant along the length of the front one-third length of the blade 70.

The lingual surface 18 is also able to be termed the "lingual" surface 18, in that this is the side of blade 70 that engages the tongue of the person being examined. The bottom or lingual surface 18, because it defines a concave cavity area, allow a person's tongue to be cradled within the concave cavity area. Since the width of the blade 70 allows the descending sides 30 and 30' to be concurrently positioned close to the edges of a person's tongue, lateral movement of the person's tongue in relation to the blade 70 is prevented. In addition, the side area of a person's tongue do not readily begin protruding around side 30 or 30', so as to interfere with any viewing of a person's throat and/or airway, during the examination or insertion of equipment.

The degree of curvature exhibited by lingual surface 18, as defined between side 30 and 30' is sufficient to create a cavity for the placement and retaining of a tongue, where the depth of said cavity is approximately 0.5 cm, when using a blade 70 that is approximately 2 cm wide. Said cavity is shown in FIG. 5 and defined as the area numbered 55. The shape of cavity 55 approximates the top surface of a patient's tongue. A tongue, when positioned in cavity area 55, is able to retain its normal shape, and therefore is not prone to flatten out during the examination.

Side edges 30 and 30', since they protrude downward, will apply a squeezing pressure to be top side of a person's tongue, so that during examination, the downward pressure applied by side 30 and side 30' will cause the mass of the tongue to automatically move upward into cavity area 55. When a patient's tongue remains flattened, so that it protrudes beyond side edge 30 and side edge 30', the tongue will virtually be unable to wrap around blade 70 sufficiently so as to block the necessary view along the length of blade 70.

Referring also to FIGS. 7, 8, 9, and 10, a laryngoscope blade 71 is shown, where the length of said blade 71 is shorter then the blade 70 shown in FIG. 3. In this particular laryngoscope 10, the blade 71 has a width similar to that shown in FIG. 3. For purposes of this FIG. 7, the width of blade 71 is approximately 2.0 cm. The overall length of blade 71 is approximately 7.5 cm. The base end 23 of blade 71, since it has the same width as blade 70, will cover a coupling 12 having a width of two centimeters or less.

In FIG. 10, flange 30 is oriented in the same fashion as flange 20 is in FIG. 6. Guide flange 26, is likewise oriented in the same manner as guide flange 16 in FIG. 6. Flange 30 and guide flange 26 should preferably have a length of approximately 65 percent of the total length of blade 71. Therefore, it blade 71 has a length of approximately of 7.5 centimeters, the flange 30 and guide flange 26, should be defined along approximately 5 cm of the total length of blade 71, beginning at the base end 23 of blade 71.

Referring also to FIG. 9, a cross sectional view of blade 71 is shown, as would be defined along plane 61 in FIG. 7. The dimensions and description of FIG. 9, mirror those as discussed for FIG. 5.

Referring now to FIG. 11, a blade 72, having a similar length as that of blade 71 shown in FIG. 7, is depicted. This type of laryngoscope 10, has both a shorter blade 72 than blade 70 in FIG. 3, and also has a narrower width from side 30 to side 30' then blade 71 shown in FIG. 7. Use of blade 72 is preferable when examining children, as they have smaller airway passages than do adults.

The approximate dimensions of the laryngoscope 10, as shown in FIGS. 11 through 14, are simply defining a laryngoscope 10 of a smaller scale then that depicted in FIGS. 3 through 6. Blade 72 has an approximate length of 7.5 cm from its base in 33 to its curved front end 35. Where blade 72 is placed on coupling 12, where coupling 12 has the same width and dimensions as shown in FIG. 6 and FIG. 10, the blade will not completely cover the top side of coupling 12, as it is shown in FIG. 14. The base end 33 of blade 72 exhibits a slight curvature which is more greatly enhanced towards the curved front end 35 of blade 72. FIG. 14 shows that the flange 40 and guide flange 46 are similar to flange 30 and guide flange 26, as shown in FIG. 10, both in size and length.

Referring now to FIG. 13, a cross sectional view of blade 72 is shown, as would be defined along plane 62. On this smaller blade 72, the distance from side 30 to side 30' would be approximately 1.5 cm, and would define a slightly smaller cavity 56 then the cavity 55 as shown in FIG. 5 and FIG. 9. When used with children, who would generally have smaller tongue cavity 56 provides the same area for the patient's tongue to be cradled within.

The degree of curvature for blade 70 is shown in FIG. 4, in which the thickness of the blade 70 indicates the amount of curvature across the width of blade 70. The thickness of blade 70 is preferably uniform. As it is shown in FIG. 4, a slight curvature of blade 70 exists at base and 13, and increases in curvature dimensions along the length of said blade 70, moving from base end 13 to the curved front end 15.

The degree of curvature for blade 71 is shown in FIG. 8, in which the thickness of the blade 71 indicates the amount of curvature across the width of blade 71. The thickness of blade 71 is preferably uniform. As it is shown in FIG. 8, a slight curvature of blade 71 exists at base end 23, and increases in curvature dimensions along the length of said blade 71, moving from base end 23 to the curved front end 25.

The degree of curvature for blade 72 is shown in FIG. 12, in which the thickness of the blade 72 indicates the amount of curvature across the width of blade 72. The thickness of blade 72 is preferably uniform. As it is shown in FIG. 12, a slight curvature of blade 72 exists at base and 33, and increases in curvature dimensions along the length of said blade 70, moving from base end 33 to the curved front end 35.

Figure 15:
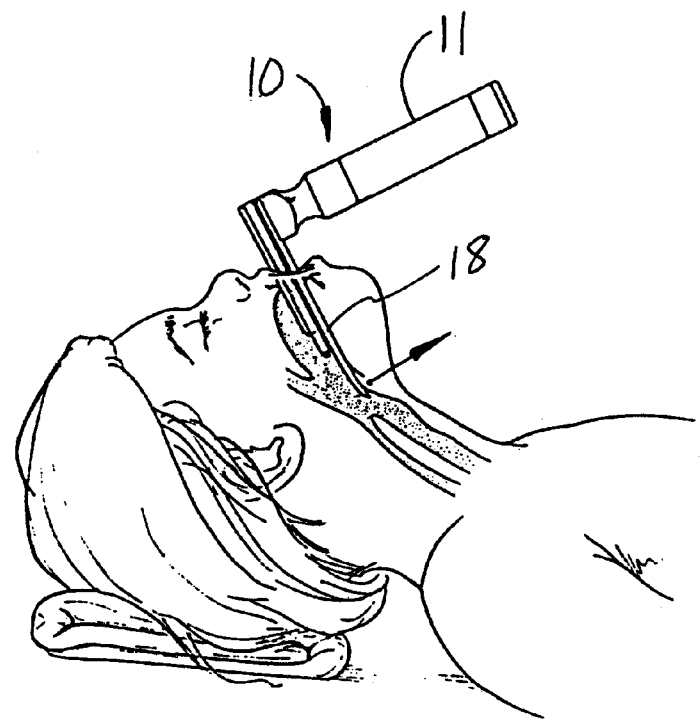
FIG. 15 is a side view of the laryngoscope being used on a patient.

Referring now to FIG. 15, a laryngoscope 10 is shown, as used during examination of a patient. During the use of the laryngoscope 10, the patient is generally laying down, and examination taking place in the manner shown. The lingual surface 18, also referred to as the lingual side, presses against the patient's tongue, and urges the tongue upward, so as to establish a proper view.

For final clarification, referring also to FIG. 16, the blade 70 is shown in perspective, with the palatal surface 14, bottom (also referred to as lingual) surface 18, and the concave surface defined by the concave bottom (also referred to as lingual) surface 18 shown.

From the foregoing statements, summary and description in accordance with the present invention, it is understood that the same are not limited thereto, but are susceptible to various changes and modifications as known to those skilled in the art and we therefore do not wish to be limited to the details shown and described herein, but intend to cover all such changes and modifications which would be encompassed by the scope of the appended claims.

I claim:

1. An improved laryngoscope blade, able to oriented with regard to a coupling, where said laryngoscope blade comprises:
   a. A base end, that is capable of being attached to a coupling, so that the base and coupling are rigidly fixed and oriented to one another;
   b. A blade having a width defined by a first side and a second side, where the blade has a palatal surface and a lingual surface, where the lingual surface of the blade defines a concave bottom lingual side, so that when the blade is used during examination of a patient's airway, the concave surface will press against the top side of a patient's tongue; and
   c. A curved front end.

2. An improved laryngoscope blade, able to be oriented with regard to a coupling, as recited in claim one, where the thickness of the blade is uniform along the length and width of said blade.

3. An improved laryngoscope blade, able to be oriented with regard to a coupling, as recited in claim one, where the bottom lingual surface defines a cavity, with the sides of said blade descending downwards to define the cavity, so that when the blade is pressed against a patient's tongue, the side edges will urge the tongue into the cavity.

4. An improved laryngoscope blade, able to be oriented with regard to a coupling, as recited in claim one, where the degree of curvature across the width of the blade increases along the length of the blade from the base end, toward the curved front end.

5. An improved laryngoscope blade, able to be oriented with regard to a coupling, as recited in claim one, where the blade supports a flange and guide flange, which assist in guiding tubes and holding a light.

6. An improved laryngoscope blade, able to be oriented with regard to a coupling, as recited in claim one, where the blade has a length that can vary from 6.5 centimeters to 10 centimeters, and a width varying from 1.5 centimeters to 2.0 centimeters.

7. An improved laryngoscope blade, having a top side with defined by two parallel sides, where the width of the blade defines a concave bottom lingual surface, where the concave area defines a cavity having a shape that approximates the palatal surface of a patient's tongue, so that when a tongue is positioned in the cavity area, defined by the blade, the tongue is able to retain its normal shape.

\* \* \* \* \*